United States Patent [19]

Densky

[11] Patent Number: 4,717,343
[45] Date of Patent: Jan. 5, 1988

[54] METHOD OF CHANGING A PERSON'S BEHAVIOR

[76] Inventor: Alan B. Densky, 2060 Collier Ave., Suite 14, Ft. Myers, Fla. 33901

[21] Appl. No.: 880,551

[22] Filed: Jun. 30, 1986

[51] Int. Cl.⁴ .............................................. G09B 19/00
[52] U.S. Cl. ................................... 434/236; 434/262; 352/85; 352/91 R
[58] Field of Search .............................. 434/236–238, 434/262, 322, 333; 352/41, 42, 85, 91 R, 91 C, 91 S

[56] References Cited

U.S. PATENT DOCUMENTS

| | | | |
|---|---|---|---|
| 1,921,963 | 8/1933 | Crabtree | 369/285 |
| 2,133,085 | 10/1938 | Draper | 352/44 |
| 2,517,246 | 8/1950 | Seitz | 352/42 |
| 3,278,676 | 10/1966 | Becker | 358/142 |
| 3,545,849 | 12/1970 | Miheles | 352/45 |
| 3,782,006 | 1/1974 | Symmes | 434/234 |
| 3,905,701 | 9/1975 | David | 355/71 |
| 4,181,410 | 1/1980 | Sicha et al. | 352/91 R |
| 4,200,364 | 4/1980 | Borowski et al. | 352/141 |
| 4,483,681 | 11/1984 | Weinslatt | 434/236 |

FOREIGN PATENT DOCUMENTS 1557773  2/1969  France ................................ 434/236

*Primary Examiner*—John E. Murtagh
*Assistant Examiner*—Andrew Joseph Rudy
*Attorney, Agent, or Firm*—Merrill N. Johnson

[57] ABSTRACT

A method of conditioning a person's unconscious mind in order to effect a desired change in the person's behavior which does not require the services of a trained therapist. Instead the person to be treated views a program of video pictures appearing on a screen. The program as viewed by the person's unconscious mind acts to condition the person's thought patterns in a manner which alters that person's behavior in a positive way.

7 Claims, No Drawings

METHOD OF CHANGING A PERSON'S BEHAVIOR

BACKGROUND OF THE INVENTION

The present invention relates to methods for conditioning a person's unconscious thought patterns by having the person view a program of video pictures projected upon a screen in order to alter that person's behavior.

It is well established in medicine and science that the human mind operates on two planes, the conscious and the unconscious. That part of the human mind used for reasoning and communicating with full awareness by the individual and which also controls voluntary behavior such as talking and walking is called the conscious mind. The unconscious mind, sometimes referred to as the subconscious, controls those functions which take place without the person's awareness such as heartbeat, breathing, glandular action, and such involuntary reactions as appetite, tension and pain.

Hypnosis was one of the first techniques used to reach a person's unconscious mind. In the late 1800's hypnosis was used to trigger the release of the endorphins, an opiate-like substance manufactured and stored within the brain, to serve as anesthesia during surgery. More recently, hypnosis has been used to effect appetite control, smoking abatement, reduction of stress and depression, and painless childbirth. During the first half of the 1900's Dr. Milton Erickson introduced the use of structured linguistic patterns in hypnotic therapy.

In the early 1970's Richard Bandler and John Grindler pioneered neuro-linguistic programming in which the therapist auditorially (by voice) tells the patient to complete a certain mental exercise in his mind's eye in order to bring about behavioral change at the unconscious and conscious levels of the patient's mind.

Both hypnosis and neuro-linguistic programming are methods of conditioning a person's thought processes through sounds transmitted by voice.

Another method of affecting an individual's unconscious thought processes is subliminal suggestion. Audio subliminals consist of a human voice repeating auditory suggestions over and over, and the voice is "covered over" by a sound such as ocean waves which is the only sound the conscious mind hears. But the unconscious hears the voiced suggestions. Video subliminals inject written messages (such as "buy popcorn") at a rate of about one frame per second into a moving picture film. There are 24 frames per second in the standard movie or video and thus the subliminal message registers only on the unconscious mind. One suggested use of video subliminal suggestion is set forth in U.S. Pat. No. 3,278,676 granted Oct. 11, 1966.

Suggestions have also been made to use visual displays projected upon a screen as an addition to audio signals, electric shock signals or other sensory messages to assist a person to build up an aversion to an undesirable habit. One such suggestion is set forth in U.S. Pat. No. 3,782,006 granted Jan. 1, 1974.

SUMMARY OF THE INVENTION

Most prior methods intended to reach a person's unconscious mind in order to effect a desired change in the person's habits require a trained therapist—a hypnotist or psychologist—to administer the program. Thus such methods are both expensive and limited by the number of specially trained therapists available to administer the programs.

I have invented a unique method for conditioning a person's unconscious mind in order to effect a desired change in the person's behavior which does not require a trained therapist. Instead, the person to be treated views a program of video pictures projected upon a screen. Although the pictures appearing on the screen are viewed by the person's conscious as well as unconscious mind, the program's images as viewed act to condition the person's unconscious thought patterns in a way which serves to alter that person's behavior.

Since it is usually a picture or image within a person's mind that creates the behavior and feeling a person will experience, my method programs the person's mind so that certain undesirable mental images in that person's conscious and/or unconscious mind (at the time of treatment and thereafter) will be automatically exchanged in the mind for a desirable mental image. When the mind thus exchanges mental images that person will experience a positive change in feelings and behavior.

My method of video programming uses two related but different techniques that I have named the Flash and the Chop, which are preferably viewed in sequence by the person being programmed.

The Flash is designed to set up new stimulus-response patterns in the brain. The person viewing the sequences of the Flash has his or her mind programmed to automatically replace a specific undesirable image when it appears with a desirable image. For example, should a stressful thought or mental image come into the person's mind, it will trigger a relaxing thought or a mental image of a relaxing scene.

By lengthy experimentation, I have determined the time of exposure and sequence of the scenes which comprise the Flash and which give it its power to program the human mind. The exact number of times the Flash is repeated will depend upon the nature of the program.

Basically, the sequence of views comprising the Flash includes two different pictures which I have named the cue picture and the outcome picture. The cue picture is a picture or image which may be either still or moving and which stimulates in the mind of the viewer an undesirable behavioral response. The outcome picture triggers a desired response.

The Flash comprises the following sequence of views:

1. Start with the cue picture in bright color, focused sharply and as large as possible. Hold the cue picture on the screen for a few seconds.

2. If the cue picture is a movie, have the movie go still and have the picture slowly recede (move away) gradually appearing smaller.

3. After a few seconds of the picture moving away, have the picture go from color to black and white.

4. After a few more seconds of the picture moving away, blur the picture.

5. After a few more seconds, the black and white blurred cue picture disappears by receding into the center of the screen.

6. Slowly bring the outcome picture into view from the same spot where the cue picture disappeared. The picture is still, small, blurred and in black and white but gradually gets larger and becomes sharply focused.

7. After a few more seconds, the picture gets larger and appears in color.

8. After a few more seconds, the picture fills the entire screen in bright color.

9. If the outcome picture is part of a movie, activate the movie and hold it on the screen for a few seconds.

10. Make the screen go blank white for about 5 seconds.

11. Repeat views 1 through 10 about four times.

12. Repeat views 1 through 9 about four times but with their original lapsed time cut by 50% and each time followed by the screen going blank white for about 5 seconds.

13. Repeat views 1 through 5 but with their elapsed time cut to about 6 frames.

14. Repeat views 6 through 9 but with their elapsed time cut to about 6 frames.

15. Blank white screen for about 5 seconds.

16. Repeat steps 13 through 15 several times.

17. Repeat views 1 through 5 but cut their elapsed time to about 3 frames.

18 Repeat views 6 through 9 but cut their elapsed time to about 6 frames.

19. Blank white screen for about 5 seconds.

20. Repeat steps 17 through 19 several times.

21. Finally, hold outcome picture on the screen for about 10 seconds.

In contrast to the Flash as just described, the Chop is a method of alternate viewing of two preferably moving scenes, the first showing a undesirable behavior pattern or habit of the viewer and the second showing a repulsive act or a life-threatening consequence of the first scene, to create an automatic connection between the two scenes in the conscious and unconscious mind of the viewer.

As the result of lengthy experimentation, I have determined a most effective sequence and timing of the two pictures of the Chop which give it the power to permanently program a person's mind and alter that person's habits in a desirable manner.

The Chop consists of the following sequence of viewing the two pictures described above:

1. The undesirable habit will be pictured bright and clearly focused, in color and moving or still, whichever best depicts the undesirable habit most effectively. The picture will remain on the screen about 3 seconds in order to affix in the mind of the viewer the view to be altered.

2. The repulsive scene or the scene of the life-threatening consequence of the undesirable habit preferably moving is flashed upon the screen in bright color, clearly focused in order to alter the viewer's perception of the first picture. This second picture remains on the screen for about 3 seconds.

3. The sequence of views 1 and 2 are repeated at about 3-second intervals several times.

4. View 1 will be displayed for about one second.

5. View 2 will be displayed for about one second.

6. Steps 4 and 5 will be repeated several times.

7. View 1 will be displayed for about 1/24th of a second.

8. View 2 will be displayed for about 1/24th of a second.

9. Steps 7 and 8 will be repeated several times.

The foregoing sequence of views will be most effective when the Chop is followed by one or more "Chop scenes" which repeat the first picture but the second picture is replaced by another repulsive or life-threatening picture.

I have found excellent results are achieved by having the person view in one session of about one-half hour a program consisting first of several different Flash sequences followed by several Chop scenes each with a different second picture.

DETAILED DESCRIPTION OF THE PREFERRED EMBODIMENT

I have used a preferred embodiment of my method of conditioning a person's unconscious mind to effect a desired change in the person's behavior. The preferred embodiment which I call Neuro-Vision ™ has been successfully used to cause several dozens of habitual smokers to give up their smoking habit.

The only treatment these habitual smokers underwent was to view a program lasting approximately 30 minutes displayed upon a screen consisting of six different Flash scenes followed by five successive Chop scenes as hereinafter described. No preliminary or subsequent treatment by a hypnotist, psychologist or other trained therapist was required.

The six Flash scenes of my Neuro-Vision ™ program are viewed in the following order:

Flash Scene 1: The cue picture consists of the words STRESS, PROBLEMS and WORRY listed one above the other in large red block letters on a bright white background. The outcome picture consists of the words PEACE, SECURITY and TRANQUILITY listed one above the other in large blue block letters on a bright white background.

Flash Scene 2: The cue picture consists of the words STRESS, PROBLEMS and WORRY listed one above the other in large red block letters on a bright white background. The outcome picture consists of a palm tree blowing in a gentle breeze at sunset on a sandy beach.

Flash Scene 3: The cue picture is viewed with the camera as the eyes of a person viewing a burning cigarette in his hand resting on a table which also contains an ashtray and a cup of coffee and the picture also includes a portion of a newspaper being read by the person. The outcome picture is essentially the same as the cue picture but without the burning cigarette and the ashtray, thus picturing a comfortable non-smoker reading his newspaper and drinking a cup of coffee.

Flash Scene 4: The cue picture is viewed with the camera as the eyes of a person viewing a burning cigarette in his hand resting on a table top containing an ashtray, cans of beer and poker chips with two other people at the table smoking and playing poker. The outcome picture is essentially the same as the cue picture but the person's hand has no cigarette and no ashtray near him; his side of the table is clean as he plays cards while the other two players are still smoking.

Flash Scene 5: The cue picture is viewed with the camera as the eyes of a person driving a car viewing his hands on the steering wheel with a burning cigarette in one hand. The cue picture is a side view of a comfortable non-smoker driving his car.

Flash Scene 6: The cue picture is viewed with the camera as the eyes of a person viewing his hand holding a burning cigarette as he watches a television program in the background. The outcome picture is a profile view of a comfortable non-smoker watching television.

Each of the Flash Scenes 1 through 6 is displayed in the following sequence:

1. Hold the cue picture on the screen for three seconds.

2. If the cue picture is a movie, have the movie go still and have the picture slowly recede and gradually get smaller.

3. After two seconds of the picture moving away, have the picture turn from color to black and white.

4. After two seconds, blur the picture.

5. After three more seconds the black and white blurred cue picture disappears by receding into the center of the screen.

6. Slowly bring the outcome picture into view from the center of the screen. The picture is still, small, blurred and in black and white but over a two second interval the picture becomes clear and grows larger.

7. For two more seconds the picture gets larger and turns into color.

8. Within two more seconds the picture fills the screen in bright color.

9. The outcome picture turns into a movie for four seconds.

10. The screen goes blank white for five seconds.

11. Repeat views 1 through 10 four times.

12. Repeat views 1 through 9 four times but with their elapsed time cut by 50% and each time followed by the screen going blank white for five seconds.

13. Repeat views 1 through 5 but with their elapsed time cut to six frames.

14. Repeat vies 6 through 9 but with their elapsed time cut to six frames.

15. Blank white the screen for five seconds.

16. Repeat steps 13 through 15 four times.

17. Repeat views 1 through 5 but cut their elapsed time to three frames.

18. Repeat views 6 through 9 but cut their elapsed time to six frames.

19. Blank white the screen for five seconds.

20. Repeat steps 17 through 19 four times.

21. Hold the outcome picture on the screen for ten seconds.

Following these six Flash scenes are five Chop scenes in each of which the first picture is a moving picture of a burning cigarette in bright color, sharply focused and filling the entire screen. And in each of the five Chop scenes the second picture is also a moving picture in color, sharply focused and filling the entire screen.

In Chop Scene 1 the second picture is a close-up of a person vomiting into an open toilet bowl.

In Chop Scene 2 the second picture is a close up of human excrement dropping into an open toilet bowl.

In Chop Scene 3 the second picture is detailed view of a caesarean section operation or the removal of a diseased lung.

In Chop Scene 4 the second picture is a person whose face is blurred sitting in a wheelchair and coughing.

In Chop Scene 5 the second picture is a mouse eating cheese.

Each of Chop Scenes 1 through 5 are displayed in the following sequence:

1. The first picture (always a burning cigarette) is displayed for three seconds.

2. The second picture is displayed for three seconds.

3. The sequence of views 1 and 2 is repeated three times.

4. The first picture is displayed for one second.

5. The second picture is displayed for one second.

6. The sequence of views 4 and 5 is repeated nine times.

7. The first picture is displayed for 1/24th of a second.

8. The second picture is displayed for 1/24th of a second.

9. The sequence of views 7 and 8 is repeated approximately 200 times or for about 18 seconds.

All display times listed above may be varied and the exact number of times the scenes are repeated may also be varied without departing from the scope of my method for conditioning a person's unconscious mind. Those psychologists, hypnotists and other therapists skilled in the art will be able to make changes in the Flash and Chop scenes for use in fields other than smoking abatement without departing from my method of programing a person's mind. It is to be understood that despite the foregoing description of the preferred embodiment of my invention called Neuro-Vision TM, the scope of my invention is defined only by the appended claims.

I claim:

1. A method of relieving a person of an undesirable habit by having that person view a program of pictures projected onto a screen, said program including the following sequence:
    (a) a bright, clear first picture in color filling the screen and designed to cause a stressful thought in the mind of the person for approximately three seconds,
    (b) then causing that first picture to gradually become blurred and smaller and become only black and white and finally shrink to a pinpoint at the center of the screen and disappear over a period of approximately six seconds,
    (c) then out of the center of the screen causing a second picture to appear which is originally blurred and in black and white and as the second picture gets larger it becomes colored, clear and bright during a period of approximately six seconds until it fills the entire screen, said picture designed to cause a relaxing throught and in its largest size being held on the screen for a period of approximately three seconds,
    (d) then causing the screen to go blank white for a period of approximately five seconds,
    (e) then repeating the foregoing sequence of pictures (a) through (d) several times, and
    (f) then speeding up the foregoing sequence of pictures (a) through (d) by 50% and repeating the foregoing sequence of pictures several times except that at the end of each sequence the screen goes blank white for approximately five seconds.

2. A method as set forth in claim 1 in which the first picture is one which stimulates in the mind of the person viewing the program an undesirable behavioral response and the second picture is one which stimulates a desired response.

3. A method of relieving a person of an undesirable habit by having that person view a program of pictures projected onto a screen,
    said program including a first picture showing an undesirable habit of the person viewing the program, and a second picture showing either a repulsive act or a life-threatening consequence of the habit shown in the first picture, and
    creating an automatic connection between the aforesaid two pictures in the conscious and unconscious mind of the person viewing the program by showing the two pictures in the following sequence:
        (a) the first picture is shown bright, clearly focused and in color for about three seconds;

(b) the second picture is shown bright, clearly focused and in color for about three seconds;

(c) the foregoing sequence of the first and second pictures each viewed for three seconds is repeated three times;

(d) the first picture is shown for one second;

(e) the second picture is shown for one second;

(f) the sequence of the first and second pictures each viewed for one second is repeated nine times;

(g) the first picture is displayed for 1/24th of a second;

(h) the second picture is displayed for 1/24th of a second; and (i) the sequence of the first and second pictures each viewed for 1/24th of a second is repeated approximately 200 times during a period of about 18 seconds.

4. A method as set forth in claim 1 followed by a program of pictures projected onto the screen which includes a first picture showing an undesirable habit of the person viewing the program, and a second picture showing either a repulsive act or a life-threatening consequence of the habit shown in the first picture, and creating an automatic connection between the aforesaid two pictures in the conscious and unconscious mind of the person viewing the program by showing the two pictures in the following sequence:

(a) the first picture is shown bright, clearly focused and in color for about three seconds;

(b) the second picture is shown bright, clearly focused and in color for about three seconds;

(c) the foregoing sequence of the first and second pictures each view for three seconds is repeated three times;

(d) the first picture is shown for one second;

(e) the second picture is shown for one second;

(f) the sequence of the first and second pictures each viewed for one second is repeated nine times;

(g) the first picture is displayed for 1/24th of a second;

(h) the second picture is displayed for 1/24th of a second; and (i) the sequence of the first and second pictures each viewed for 1/24th of a second is repeated approximately 200 times during a period of about 18 seconds.

5. A method of relieving a person of an undesirable habit by having the person view a program of pictures projected on a screen consisting of a first picture which stimulates in the mind of the person viewing the program an undesirable behavioral response and a second picture which stimulates a desired response, said pictures being presented in the following sequence:

(a) a bright, clear first picture in color filling the screen and designed to cause a stressful thought in the mind of the person for approximately three seconds, (b) then causing that first picture to gradually become blurred and smaller and become only black and white and finally shrink to a pin point at the center of the screen and disappear over a period of approximately six seconds, (c) then out of the center of the screen causing a second picture to appear which is originally blurred and in black and white and as the second picture gets larger it becomes colored, clear and bright during a period of approximately six seconds until it fills the entire screen, said picture designed to cause a relaxing thought and in its largest size being held on the screen for a period of approximately three seconds, (d) then causing the screen to go blank white for a period of approximately five seconds, (e) then repeating the foregoing sequence of pictures (a) through (d) several times, (f) then speeding the foregoing sequence of pictures (a) through (d) by 50% and repeating the foregoing sequence of pictures several times except that at the end of each sequence the screen goes blank white for approximately five seconds.

6. A method of relieving a person of an undesirable habit by having the person view a program of pictures projected on a screen consisting of a first picture which stimulates in the mind of the person viewing the program an undesirable behavioral response and a second picture which stimulates a desired response, said pictures being presented in the following sequence:

the first picture appears on the screen in bright color focused sharply and as large as possible, and this picture is held on the screen a few seconds, if the first picture is a movie, have the movie go still and the picture gradually recede, as it gradually recedes, the picture goes from color to black and white, as the picture continues to recede, the picture blurs, the black and white blurred first picture disappears by receding into a spot on the screen, slowly the second picture appears from the same spot on the screen where the first picture disappeared, said second picture being small, still, blurred and in black and white, and gradually over a few seconds grows larger and becomes sharply focused, after a few more seconds the second picture gets larger and appears in color, after a few more seconds the second picture fills the entire screen in bright color, if the second picture is part of a movie, activate the movie and hold it on the screen for a few seconds, make the screen go blank white for several seconds, repeat the foregoing sequence of views about four times, repeat the foregoing views several times more but with their original lapsed time cut by 50% and each time followed by the screen going blank white for about five seconds, repeat the foregoing views of the first picture but with their elapsed time cut to about six frames, repeat the foregoing views of the second picture but with their elapsed time cut to about six frames, have the screen go blank white for about five seconds, repeat several times the six frames of the first picture followed by the six frame viewing of the second picture followed by a five second interlude of blank white, and hold the second picture on the screen about ten seconds.

7. The method set forth in claim 6 followed by a program of pictures projected onto the screen which includes a first picture showing an undesirable habit of the person viewing the program and a second picture showing either a repulsive act or a life-threatening consequence of the habit shown in the first picture, and creating an automatic connection between the aforesaid two pictures in the conscious and unconscious mind of the person viewing the program by showing the two pictures in the following sequence:
(a) the first picture is shown bright, clearly focused and in color for about three seconds;
(b) the second picture is shown bright, clearly focused and in color for about three seconds;
(c) the foregoing sequence of the first and second pictures each viewed for three seconds is repeated three times;
(d) the first picture is shown for one second;
(e) the second picture is shown for one second;
(f) the sequence of the first and second pictures each viewed for one second is repeated nine times;
(g) the first picture is displayed for 1/24th of a second;
(h) the second picture is displayed for 1/24th of a second; and
(i) the sequence of the first and second pictures each viewed for 1/24th of a second is repeated approximately 200 times during a period of about 18 seconds.

* * * * *